United States Patent
Boone

(10) Patent No.: US 9,368,270 B2
(45) Date of Patent: Jun. 14, 2016

(54) PLANAR TRANSFORMER ASSEMBLIES FOR IMPLANTABLE CARDIOVERTER DEFIBRILLATORS

(71) Applicant: Medtronic, Inc., Minneapolis, MN (US)

(72) Inventor: Mark R Boone, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/471,128

(22) Filed: Aug. 28, 2014

(65) Prior Publication Data

US 2014/0368308 A1    Dec. 18, 2014

Related U.S. Application Data

(62) Division of application No. 13/524,222, filed on Jun. 15, 2012, now Pat. No. 8,830,693.

(51) Int. Cl.
| | |
|---|---|
| *H01F 5/00* | (2006.01) |
| *H01F 27/28* | (2006.01) |
| *A61N 1/39* | (2006.01) |
| *H01F 27/40* | (2006.01) |

(52) U.S. Cl.
CPC .......... *H01F 27/2804* (2013.01); *A61N 1/3981* (2013.01); *H01F 27/40* (2013.01); *H01F 2027/2809* (2013.01)

(58) Field of Classification Search
CPC .................................. H01F 5/00; H01F 27/28
USPC ................................................. 336/200, 232
See application file for complete search history.

(56) References Cited

U.S. PATENT DOCUMENTS

| | | | |
|---|---|---|---|
| 4,873,757 A * | 10/1989 | Williams | ............... 29/602.1 |
| 5,126,715 A | 6/1992 | Yerman et al. | |
| 5,990,776 A | 11/1999 | Jitaru | |
| 6,124,778 A | 9/2000 | Rowley et al. | |
| 6,476,704 B2 | 11/2002 | Goff | |
| 6,477,414 B1 | 11/2002 | Silvian | |
| 6,847,284 B2 * | 1/2005 | Gamou et al. | ................ 336/223 |
| 7,167,074 B2 | 1/2007 | Fenner et al. | |

(Continued)

FOREIGN PATENT DOCUMENTS

| | | | |
|---|---|---|---|
| JP | 03183106 A | * | 8/1991 |
| JP | 05135968 A | * | 6/1993 |

OTHER PUBLICATIONS

Boone, et al., "Wafer Level Packages of High Voltage Units for Implantable Medical Devices and Corresponding Fabrication Methods", filed Jun. 15, 2012, U.S. Appl. No. 13/524,253, 29 pages.

(Continued)

*Primary Examiner* — Tsz Chan
(74) *Attorney, Agent, or Firm* — Evans M. Mburu

(57) ABSTRACT

A planar transformer assembly, for use in charging capacitors of an ICD, includes windings arranged to minimize voltage across intervening dielectric layers. Each secondary winding of a preferred plurality of secondary windings is arranged relative to a primary winding, in a hierarchical fashion, such that the DC voltage, with respect to ground, of a first secondary winding, of the plurality of secondary windings, is lower than that of a second secondary winding, with respect to ground, wherein the first secondary winding is in closest proximity to the primary winding. The primary winding and each secondary winding are preferably formed on a corresponding plurality of dielectric layers.

9 Claims, 6 Drawing Sheets

(56) References Cited

U.S. PATENT DOCUMENTS

| | | | |
|---|---|---|---|
| 7,199,569 B1* | 4/2007 | Nakahori | 323/355 |
| 7,225,018 B2 | 5/2007 | Iverson et al. | |
| 7,292,126 B2 | 11/2007 | So | |
| 7,671,714 B2 | 3/2010 | Tiemeijer | |
| 2002/0011807 A1 | 1/2002 | Kobayashi et al. | |
| 2004/0042240 A1* | 3/2004 | Takeshima et al. | 363/74 |
| 2005/0230837 A1 | 10/2005 | Taghizadeh-Kaschani | |
| 2005/0242916 A1* | 11/2005 | So | 336/200 |
| 2008/0094164 A1 | 4/2008 | Hsu | |
| 2010/0265023 A1 | 10/2010 | Bertilsson | |
| 2010/0301985 A1* | 12/2010 | Luo | H02M 7/103 336/221 |
| 2011/0037405 A1* | 2/2011 | Suganuma et al. | 336/200 |

OTHER PUBLICATIONS

Askarinya et al., "Power Sources Suitable for Use in Implantable Medical Devices and Corresponding Fabrication Methods", filed Jun. 15, 2012, U.S. Appl. No. 13/524,304, 15 pages.

Askarinya, et al., "Integrated Circuit Packaging for Implantable Medical Devices", filed Jun. 15, 2012, U.S. Appl. No. 13/524,368, 21 pages.

* cited by examiner

PLANAR TRANSFORMER ASSEMBLIES FOR IMPLANTABLE CARDIOVERTER DEFIBRILLATORS

CROSS-REFERENCE TO RELATED APPLICATION

The present application is a divisional application of U.S. patent application Ser. No. 13/524,222, which is entitled PLANAR TRANSFORMER ASSEMBLIES FOR IMPLANTABLE CARDIOVERTER DEFIBRILLATORS, incorporated herein by reference.

FIELD OF THE DISCLOSURE

The present invention pertains to planar transformer assemblies, and, more specifically, to configurations thereof that are particularly suitable for incorporation in shocking circuits of implantable cardioverter defibrillators (ICD's) as flyback transformers.

BACKGROUND

ICD's are designed to detect atrial and/or ventricular fibrillation and, in response to the detection, to deliver high voltage shock therapy in order to terminate the fibrillation. FIG. 1 is a schematic showing a typical subcutaneous pectoral placement of an ICD 100 in a patient 102, wherein a hermetically sealed and biocompatible canister 104 of ICD 100 houses circuitry to enable detection and therapy delivery via one or more electrical leads 106, which are coupled to the circuitry and extend distally from canister 104, through the venous system 110 and into the heart 108 of patient 102, for example, the right ventricle (RV). Those skilled in the art understand that the one or more leads 106 include sensing and defibrillation electrodes, and, in most cases, pacing electrodes as well. The electrodes of lead(s) 106 are coupled to the ICD circuitry via one or more lead connectors that terminate elongate insulated conductors of the electrodes, at a proximal end of lead(s) 106; the one or more lead connectors are plugged into a connector module 105, which is mounted on canister 104, to make electrical contact with the contained ICD circuitry via hermetically sealed feedthroughs. Canister 104, for example, formed from a Titanium alloy, is typically employed as a high voltage electrode in conjunction with a high voltage electrode of lead(s) 106 to establish an effective shocking vector for cardiac defibrillation.

FIG. 2 is a simplified block diagram of a portion of the ICD circuitry, wherein a battery 202 provides operating power to a controller 204 and to a shocking circuit 206. Controller 204, which controls the delivery of energy through the electrodes of lead(s) 106, can be any type of control circuitry suitable for determining when, where and for what duration the energy may be delivered. In order to generate a voltage, for example, approximately 750 volts or more, which is necessary to deliver defibrillation shock energy, for example, at a level in the range of 5-40 Joules, shocking circuit 206 includes a capacitor element 211. A transformer assembly 210 of shocking circuit 206 typically comprises a flyback transformer coupled between battery 202 and capacitor element 211 for incremental charging of capacitor element 211. Once capacitor element 211 is charged and called upon by controller 204, a switch 212 of shocking circuit 206 connects capacitor element 211 for the routing of a high voltage pulse through to the appropriate electrodes of ICD 100.

In the past, a conventional type of transformer assembly 210 would be constructed from components that are physically separate from one another and from other electrical components of the ICD circuitry, for example, primary and secondary windings formed around a toroid-shaped magnetic core. Because these components of the conventional transformer assembly 210 take up a relatively large amount of space within canister 104, recent efforts to reduce an overall size of canister 104, for a more comfortable implant, have focused on reducing the size of flyback transformers that are employed for charging ICD capacitors. Commonly-assigned U.S. Pat. No. 7,167,074 describes the construction of planar flyback transformer assemblies, for physical integration of the transformer with other circuitry of an ICD, wherein primary and secondary windings are embedded between opposing sides of a printed circuit board (PCB) to which a planar magnetic core is mounted (i.e. E-shaped core with legs/feet extending through openings in the PCB such that the windings are disposed thereabout). Although the embodiments of planar flyback transformers that are described in the '074 Patent can reduce the amount of space taken up by a transformer assembly, such as assembly 210 within canister 104, there is still a need for improved configurations of planar flyback transformers that are particularly suited for charging capacitors of ICD's.

SUMMARY

A planar transformer assembly for use in charging capacitors of an ICD, according to embodiments of the present invention, includes windings arranged to minimize voltage across intervening dielectric layers. The planar transformer assembly includes a primary winding and, preferably, a plurality of secondary windings to charge a corresponding number of capacitors, which are stacked in series. Each of the plurality of secondary windings is arranged relative to the primary winding, in a hierarchical fashion, such that a DC voltage, with respect to ground, of a first secondary winding, of the plurality of secondary windings, is lower than that of a second secondary winding, with respect to ground, wherein the first secondary winding is in closest proximity to the primary winding. A ratio of turns of each secondary winding to the primary winding may be approximately 10:1.

Each of the primary and secondary windings may be formed on a single dielectric layer, yet, according to some preferred embodiments, the primary winding is formed on at least first and second dielectric layers, and each secondary winding is formed on a corresponding pair of dielectric layers, separate from the at least first and second layers, such that the windings are arranged in a nested fashion, for example, as follows: a first pair of layers, on which a first secondary winding is formed, is located in between individual layers of a second pair of layers on which a second secondary winding of the plurality is formed. In some embodiments, all of the layers, on which the plurality of secondary windings of the planar transformer are formed, are located in between the first and second layers on which the primary winding of the planar transformer is formed; while, in other embodiments, the first and second layers, on which the primary winding of the planar transformer is formed, are located in between individual layers of all of the pairs of layers on which the plurality of secondary windings are formed.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
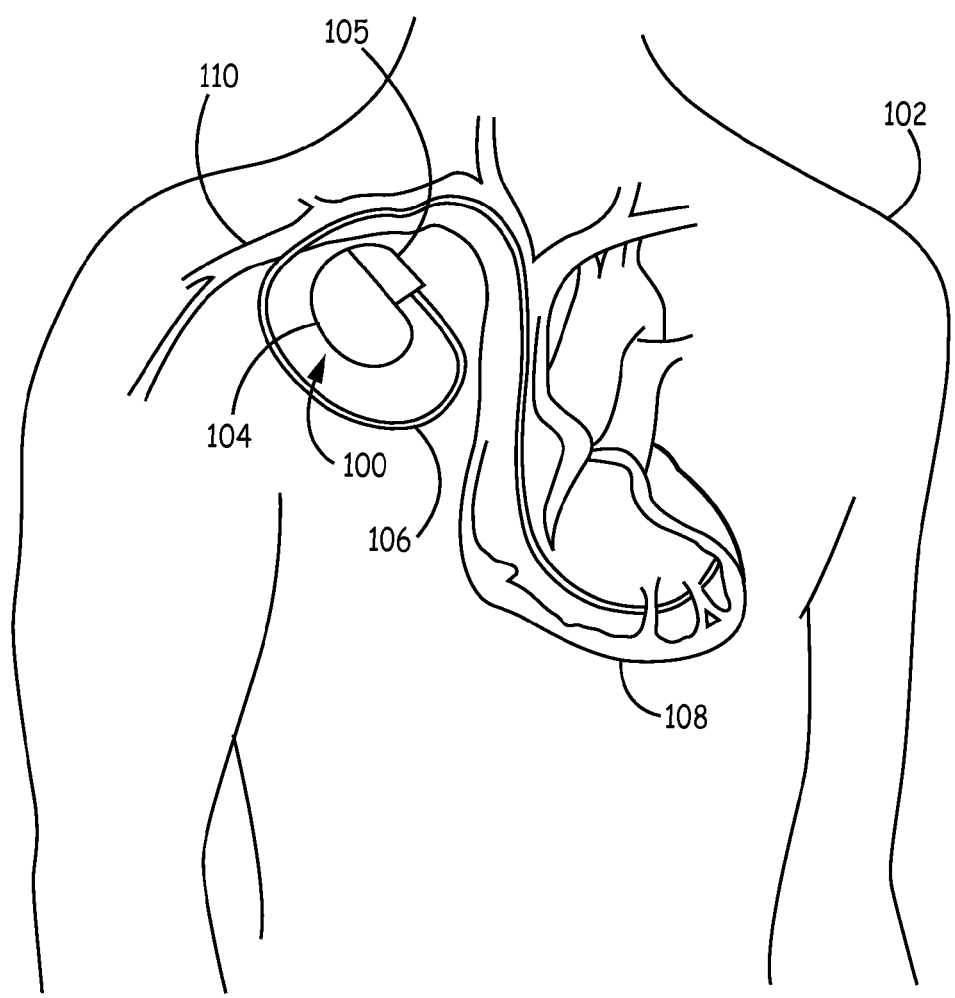
FIG. 1 is a schematic showing a typical placement of an implanted cardioverter defibrillator.
Figure 2:
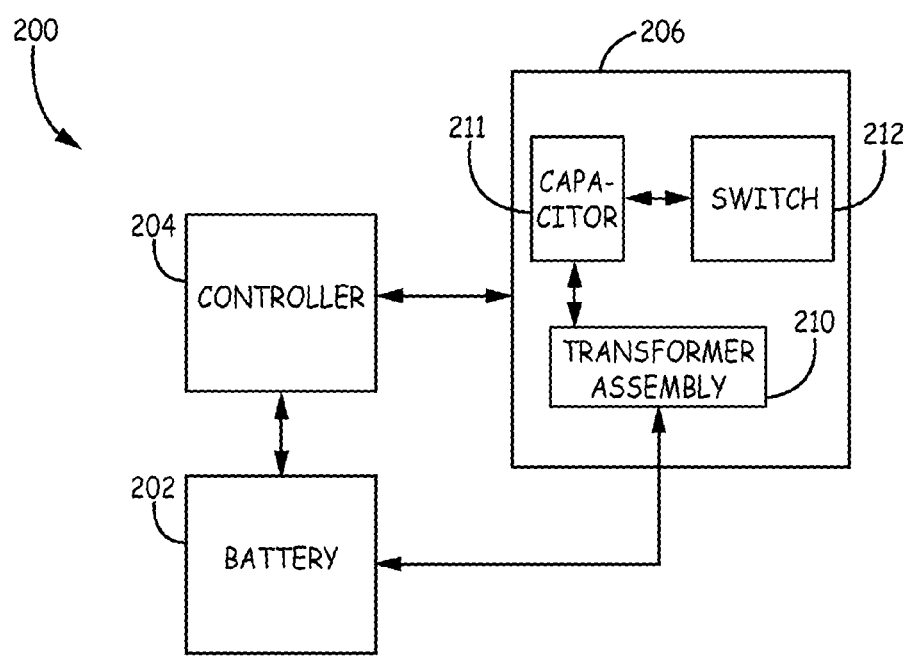
FIG. 2 is a simplified block diagram of a portion of the circuitry that may be employed by the device shown in FIG. 1.
Figure 3:
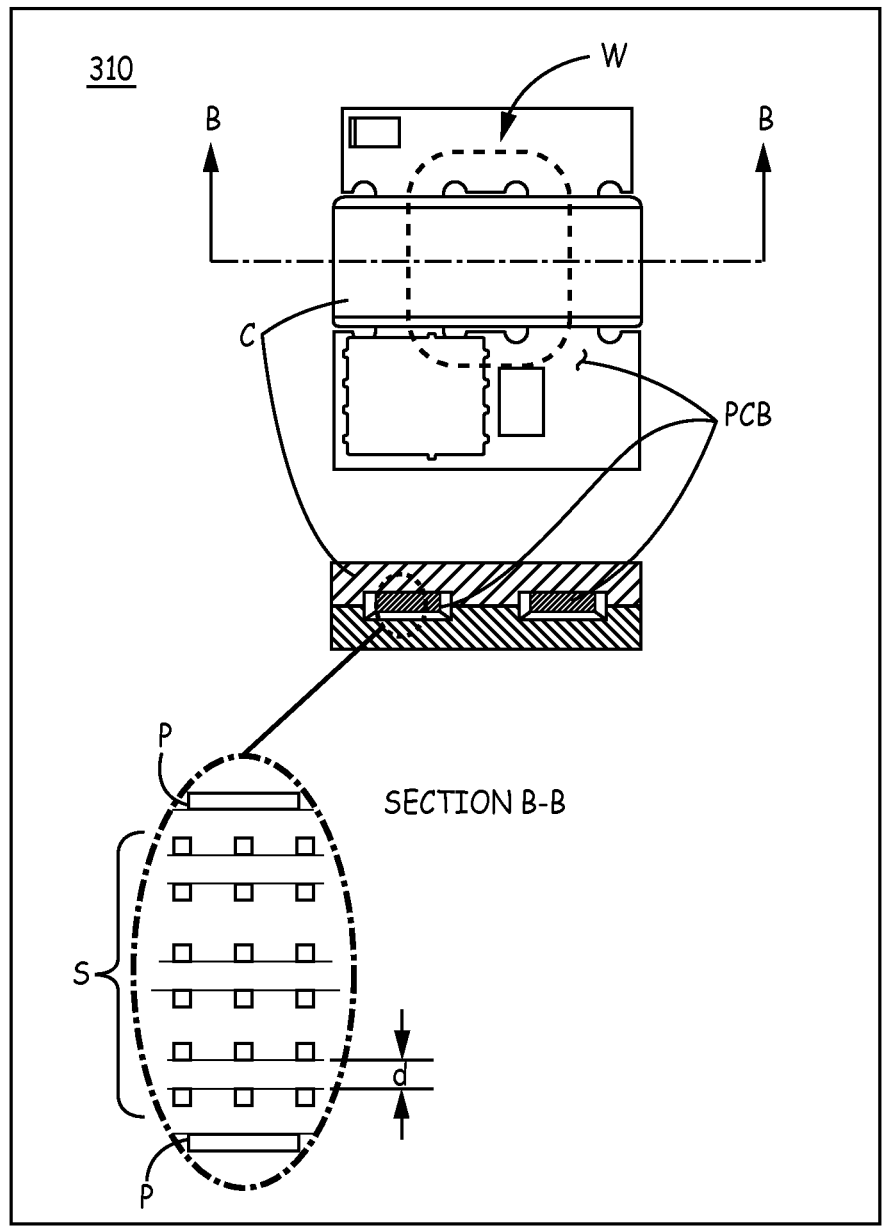
FIG. 3 is a plan view along with a corresponding cross-section view and an enlarged detail of a planar transformer assembly, according to some embodiments of the present invention.

FIG. 3 is a plan view along with a corresponding cross-section view and an enlarged detail of a planar transformer assembly 310, according to some embodiments of the present invention, which may be incorporated in shocking circuit 206 (FIG. 2), in place of the above-described transformer assembly 210. FIG. 3 illustrates assembly 310 including a multi-layer PCB, identified with reference letters "PCB", to which a planar magnetic core C is mounted. The dashed line, identified with reference letter "W", represents a general path in which primary and secondary windings P and S extend along dielectric layers of PCB with respect to legs of magnetic core C, which can be seen in the cross-section view. The enlarged detail illustrates some preferred embodiments, wherein primary winding P extends along outer layers of PCB and secondary windings S extend on layers therebetween, for example, according to the schematics of FIGS. 4A-B. It should be noted that the construction of assembly 310 may employ materials and fabrication methods known to those skilled in the art in integrated circuit fabrication. Alternately, embodiments of planar transformer assemblies may be incorporated in wafer level packages using redistributed chip packaging (RCP) fabrication methods, wherein primary and secondary windings P and S are formed in the dielectric redistribution, or routing layers of the package, for example, as described in the above-referenced U.S. patent application Ser. No. 13/524,222, which is hereby incorporated by reference, in its entirety.

Figure 4A:
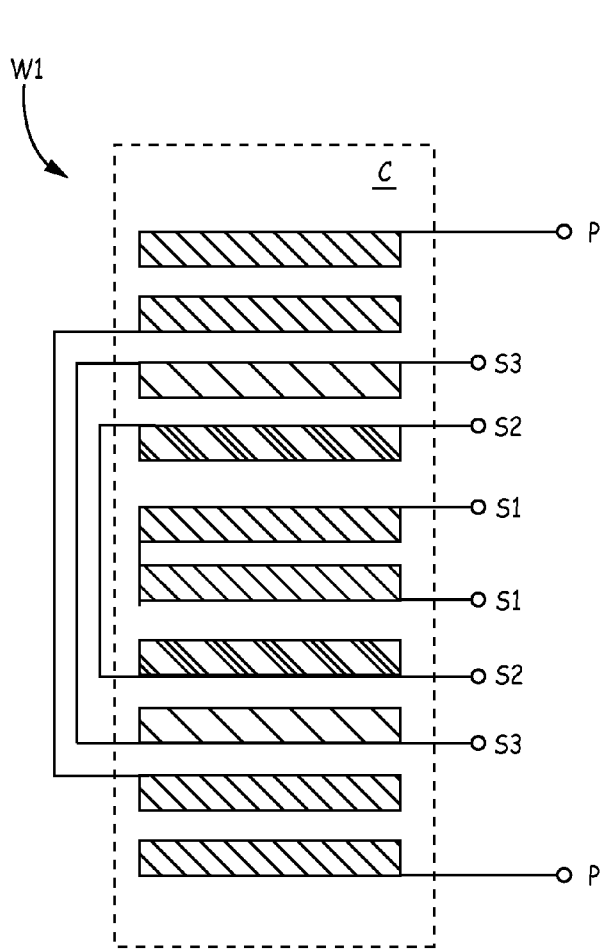
FIGS. 4A-B are two types of schematics depicting a configuration of primary and secondary windings of a planar transformer, according to some embodiments.
Figure 4B:
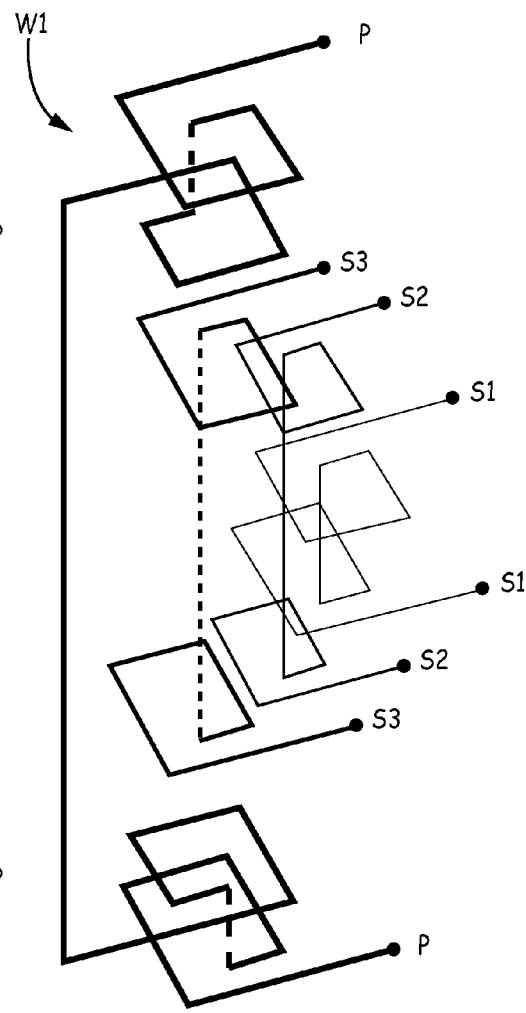

According to some preferred embodiments, capacitor 211 (FIG. 2) is made up of a plurality of storage capacitors, for example, three capacitors stacked in series, and secondary windings S are divided into a corresponding plurality of secondary windings S1, S2, S3, for individually charging each capacitor. The schematics of FIGS. 4A-B illustrate the primary winding P and each secondary winding S1, S2, S3 formed in two parts, on corresponding pairs of dielectric layers, according to some preferred embodiments, wherein the parts of each individual winding are electrically coupled, between the corresponding pair of layers, by vias. According to an exemplary embodiment, primary winding P includes one turn per layer, for example, to minimize a resistance of each turn; however, it should be noted that, if primary winding P were alternately formed on just first and second opposing outer layers, for example, to simplify fabrication of assembly 310, two turns of primary winding P may be formed on each of the first and second layers. Furthermore, it should be noted that the schematics do not illustrate an accurate turn ratio of each secondary winding S1, S2, S3 to primary winding P, which may be from approximately 7:1 to approximately 10:1, preferably approximately 10:1. The configuration of primary and secondary windings W1, in which primary winding P is formed on outer layers, may be preferred to prevent mechanical damage to narrower secondary windings S and to minimize exposure of the high voltage terminals of secondary windings S at an outer surface of PCB, for example, to prevent surface flashover.

With further reference to FIGS. 4A-B, secondary windings S1, S2, S3 are shown arranged in a nested fashion, such that a first pair of dielectric layers, on which first secondary winding S1 is formed, is located in between individual layers of a second pair of dielectric layers on which second secondary winding S2 is formed, and the pair of dielectric layers on which second secondary winding S2 is formed is located in between individual layers of a third pair of dielectric layers on which third secondary winding S3 is formed. According to the illustrated embodiment, the DC voltage of first secondary winding S1, with respect to ground (essentially the voltage of primary winding P), is greater than that of second secondary winding S2, with respect to ground, which is greater than that of third secondary winding S3, with respect to ground. Thus, the illustrated arrangement serves to minimize voltage across dielectric layers, in which the windings are embedded, when under the high voltage bias typical for ICD capacitor charging, thereby increasing a life of the dielectric material, the breakdown of which may be exacerbated by higher operating temperatures, for example, associated with size reduction of assembly 310. With reference back to FIG. 3, a typical dielectric thickness d between adjacent secondary windings S is preferably between approximately 60 micrometers and approximately 100 micrometers.

Figure 5:
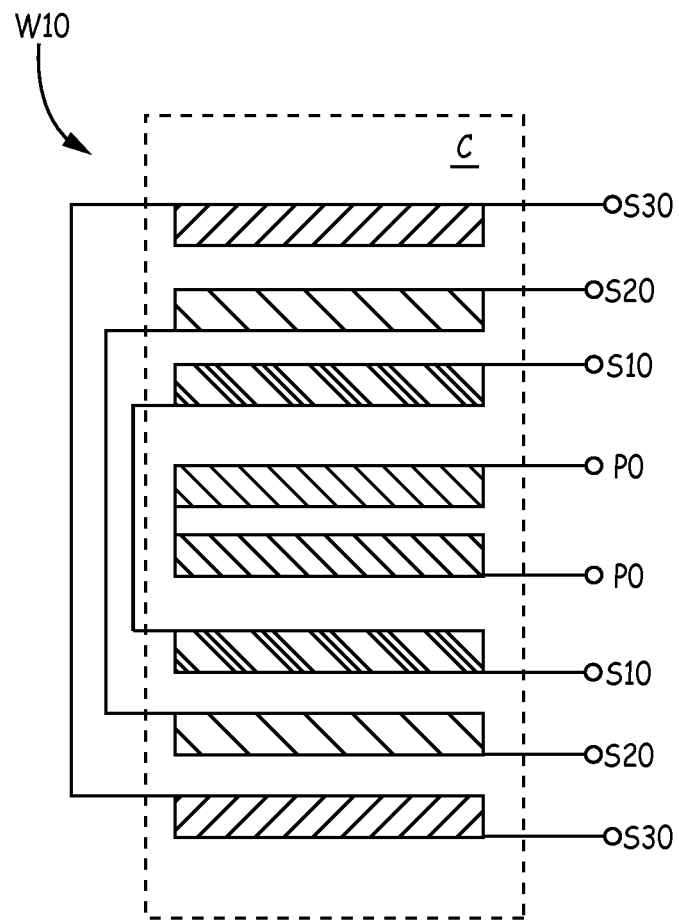
FIG. 5 is a schematic depicting a configuration of primary and secondary windings of a planar transformer, according to some alternate embodiments.

FIG. 5 is a schematic depicting an alternate configuration of primary and secondary windings W10, according to some alternate embodiments, that also minimize the voltage across dielectric layers of a multi-layer PCB, like that illustrated in FIG. 3. FIG. 5 illustrates a primary winding P0 formed on first and second layers that are located in between all the layers on which secondary windings S10, S20, S30 are formed. FIG. 5 further illustrates the formation of each secondary winding S10, S20, S30 on corresponding pairs of layers, according to some preferred embodiments, and the portions of each individual winding P, S10, S20, S30 are electrically coupled, between the corresponding pair of layers, by vias. According to the illustrated embodiment, the DC voltage of first secondary winding S10, with respect to ground, is less than that of second secondary winding S20, with respect to ground, which is less than that of third secondary winding S30, with respect to ground.

Figure 6:
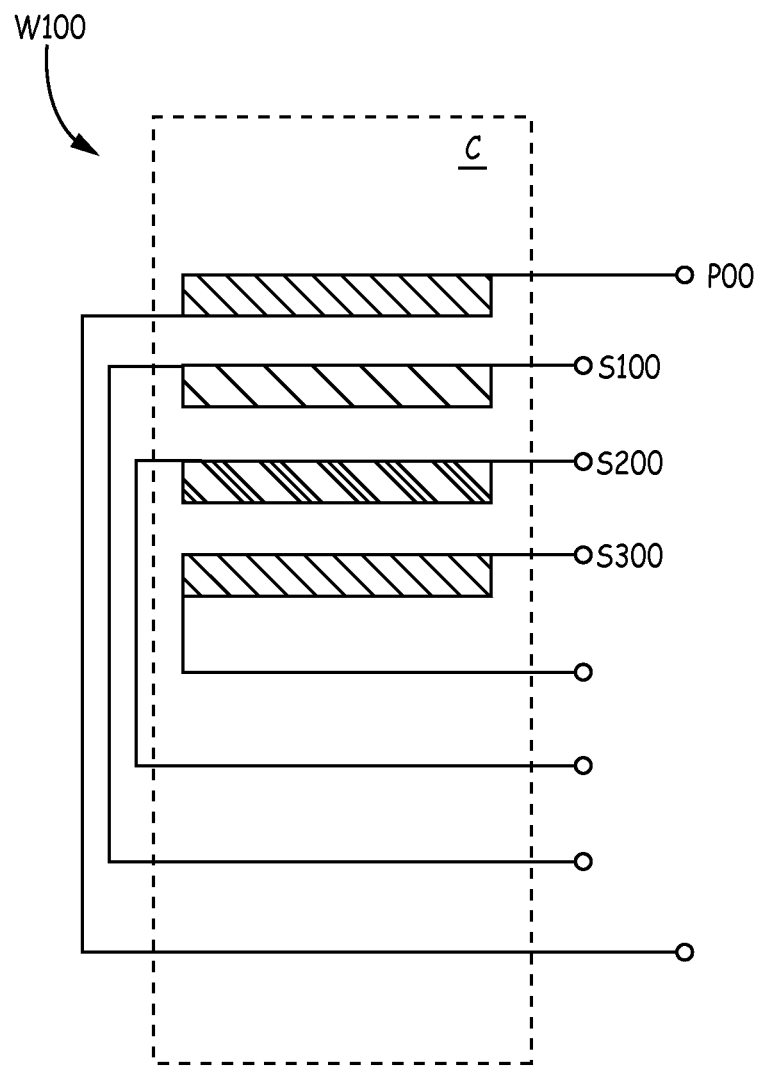
FIG. 6 is a schematic depicting yet another configuration of windings, according to some alternate embodiments.

FIG. 6 is a schematic depicting yet another configuration of windings W100, wherein an entire primary winding P00 is formed on a single dielectric layer, as is each secondary winding S100, S200, S300. With reference to FIG. 6, the plurality of secondary windings S100, S200, S300 are preferably arranged in a similar hierarchical fashion to that described above in conjunction with FIG. 4A, such that a DC voltage, with respect to ground, of first secondary winding S100 is lower than that of second secondary winding S200, which is lower than that of third secondary winding S300.

With reference to FIGS. 4A, 5 and 6, and according to exemplary embodiments, each secondary winding S1-S3/S10-S30/S100-S300 of a corresponding transformer is electrically coupled to one of three 250 volt capacitors, which are stacked in series. Prior to the start of any transformer flyback cycles, an unloaded DC voltage across each of secondary windings S1-S3/S10-S30/S100-S300 and the voltage across the capacitors is approximately 0 volts. Then, immediately prior to completion of all the flyback cycles that are necessary to fully charge the capacitors, the maximum DC voltage of secondary winding S1/S30/S300, with respect to ground, is approximately 750 volts, the maximum DC voltage of secondary winding S2/S20/S200, with respect to ground, is approximately 500 volts, and the maximum DC voltage of secondary winding S3/S10/S100, with respect to ground is approximately 250 volts.

In the foregoing detailed description, the invention has been described with reference to specific embodiments. However, it may be appreciated that various modifications and changes can be made without departing from the scope of the invention as set forth in the appended claims. For example, alternate embodiments can encompass alternative numbers of secondary windings to those illustrated.

The invention claimed is:

1. A planar transformer assembly comprising:
a primary winding having a first part and a second part that is adjacent to the first part, wherein the primary winding includes first and second opposing surfaces such that the first surface is disposed on the first part and the second surface is disposed on the second part; and
a plurality of secondary windings, the plurality of secondary windings being separated from the first and second parts of the primary winding by at least one intervening dielectric layer, and the plurality of secondary windings being separated from one another by intervening dielectric layers, wherein each of the plurality of secondary windings includes first and second portions that are disposed on the opposing first and second surfaces such that the first portion of each of the plurality of secondary windings is arranged to be spaced apart from the second portion by the primary winding, and the sequence of arrangement of each first portion of the plurality of secondary windings relative to the first surface is identical to the sequence of arrangement of each corresponding second portion of the plurality of secondary windings relative to the second surface.

2. The planar transformer assembly of claim 1, wherein a thickness of each intervening dielectric layer is between 60 micrometers and 100 micrometers.

3. The planar transformer assembly of claim 1, wherein:
the first and second parts are separated from one another across intervening dielectric layers and are connected by a via, and the first and second parts are located between the first and second portions of the plurality of secondary windings; and
the first and second portion of each secondary winding is separated from one another across corresponding intervening dielectric layers and is connected by a corresponding via.

4. The planar transformer assembly of claim 1, wherein:
the first and second portions of each secondary winding are separated from one another across corresponding intervening dielectric layers and are connected by a corresponding via; and
the first and second parts of the primary winding are separated from one another across intervening dielectric layers and are connected by a via, and the first and second parts of the primary winding are located in between the first and second parts of all of the secondary windings.

5. The planar transformer assembly of claim 1, wherein a DC voltage, with respect to ground, of a first secondary winding, of the plurality of secondary windings, is lower than that of a second secondary winding, with respect to ground, the first secondary winding being in closest proximity to the primary winding.

6. The planar transformer assembly of claim 1, wherein a turns ratio of each secondary winding to the primary winding is 10:1.

7. The planar transformer assembly of claim 1, wherein the first and second parts of the primary winding are located in between individual layers on which all of the portions of the plurality of secondary windings are formed.

8. The planar transformer assembly of claim 7, wherein a dielectric thickness between adjacent secondary windings is between 60 micrometers and 100 micrometers.

9. The planar transformer assembly of claim 1, further comprising a third surface disposed on the first part and a fourth surface disposed on the second part, wherein the adjacent first and second parts are arranged such that the third and fourth surfaces are adjacent to each other and the first and second surfaces are disposed on opposing ends of the first and second parts.

* * * * *